United States Patent [19]

Bauer

[11] 4,128,099

[45] Dec. 5, 1978

[54] SINGLE-POLE COAGULATION FORCEPS

[75] Inventor: Siegfried Bauer, Heidelsheim, Fed. Rep. of Germany

[73] Assignee: Richard Wolf GmbH, Knittlingen, Fed. Rep. of Germany

[21] Appl. No.: 835,011

[22] Filed: Sep. 20, 1977

[30] Foreign Application Priority Data

Sep. 22, 1976 [DE] Fed. Rep. of Germany ....... 2642489

[51] Int. Cl.² .............................................. A61N 3/04
[52] U.S. Cl. ............................................... 128/303.17
[58] Field of Search .................. 128/303.17, 303.13, 128/303.14, 303.15, 303.16, 407, 408, 409

[56] References Cited

U.S. PATENT DOCUMENTS

| 1,731,069 | 10/1929 | Herman | 128/303.16 |
| 1,841,968 | 1/1932 | Lowry | 128/303.14 |
| 3,805,791 | 4/1974 | Seuberth et al. | 128/303.14 |
| 3,920,021 | 11/1975 | Hiltebrandt | 128/303.17 |
| 4,024,869 | 5/1977 | Bonnet | 128/303.15 |

FOREIGN PATENT DOCUMENTS 2415263  10/1975  Fed. Rep. of Germany ...... 128/303.17

Primary Examiner—Lee S. Cohen
Attorney, Agent, or Firm—Kinzer, Plyer, Dorn & McEachran

[57] ABSTRACT

A single pole coagulation forceps comprising jaw elements operated by a traction rod passing through an externally insulated electrically conductive guide barrel, the jaw elements being electrically connected to said barrel and the traction rod comprising two parts which are insulatingly interconnected by an insulating body which is axially slidable in a cavity in an insulating sleeve which is stouter than said barrel and in which said barrel terminates proximally.

6 Claims, 8 Drawing Figures

SINGLE-POLE COAGULATION FORCEPS

BACKGROUND OF THE INVENTION

1. Field of the Invention

The invention relates to a single-pole coagulation forceps for endoscopy, and more particularly to such forceps having a traction rod which can be moved axially by means of a proximal handle, which passes with a seal at the proximal end through a guide barrel which can be connected to a high frequency (HF) terminal for HF electric current and which is provided at the distal end with jaws which can be opened and closed by means of the traction rod and which have an electrically conductive connection to the guide barrel, the guide barrel being provided with external insulation.

2. Description of the Prior Art

In a known single-pole coagulation forceps of the kind described above disclosed in German Gebrauchsmuster No. 7,513,534, the maximum possible security against the accidental transmission of HF current to the body of the patient from a point along the guide barrel for the traction rod, which is connected to HF voltage, is achieved by means of the external insulation. Even though in the known design the proximal handle section, i.e. the traction rod and the handle, is insulated, pores in the insulation may allow current to be transmitted to the doctor performing the treatment, with the result that the doctor may suffer burns since he is using the coagulation forceps in conjunction with an endoscope and has his head and eyes in the immediate vicinity of the proximal end of the forceps.

The main object of the present invention is therefore, in single-pole coagulation forceps for endoscopy, to prevent HF current from being transmitted to the patient from the guide barrel for the coagulation forceps, also to provide satisfactory protection for the doctor performing the treatment.

SUMMARY OF THE INVENTION

To this end, in a single-pole coagulation forceps as described above, the guide barrel is terminated proximally in the distal end of a shouter or thicker insulating cylinder or sheath of any desired outer circumference which has in a more proximal position an elongated cavity in which an elongated insulating body is displaceable axially, the ends of the traction rod, which is divided at this location, being fastened in the ends of the elongated body.

As a result of the traction rod being divided in this way and of the insulation between the divided ends there is at no time any current to the actuating end and the handle, with the result that the doctor is no longer exposed to the risk of facial burns.

DESCRIPTION OF THE PREFERRED EMBODIMENTS

Figure 1:
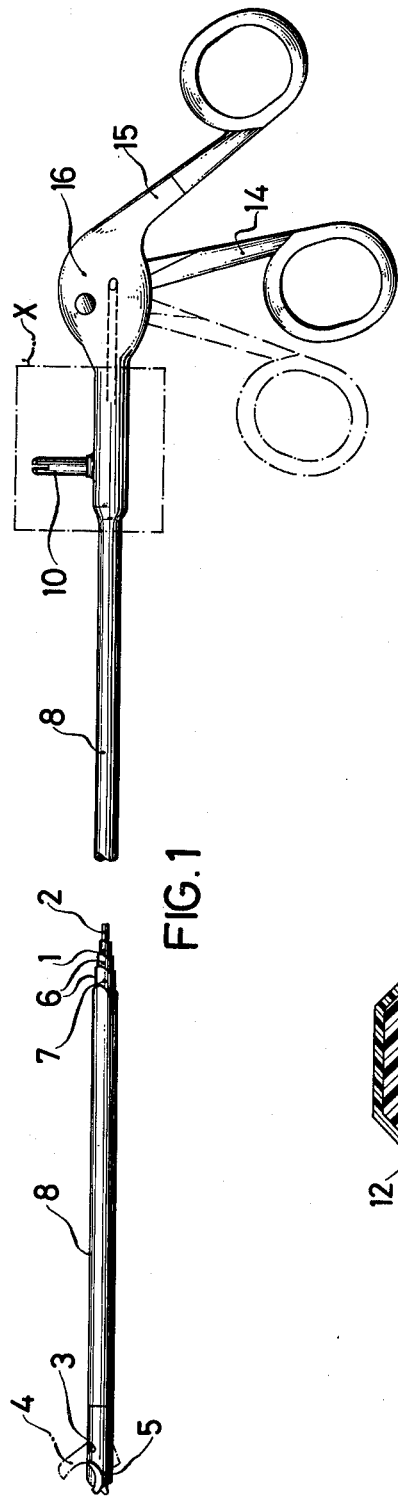
FIG. 1 is a reduced-scale, interrupted side view of a single-pole coagulation forceps constructed according to the invention.

The coagulation forceps illustrated in FIGS. 1 to 5 includes an electrically conductive guide barrel 1 of metal for an axially displaceable electrically conductive rod 2 of metal. The rod 2 passes through the barrel and distally it may form an expanding pair of jaws for example or, by its axial displacement, it may cause a jaw 4 to open and close via a pivot connection 3, the other jaw 5 being rigidly connected to the barrel 1. Alternatively, by arranging for a suitable connection, the two jaws 4, 5 may be made to move symmetrically to one another. The barrel 1 is provided in a known manner with an insulating coating or a thin sheath 6 of plastics material, e.g. a shrink sleeve, which is enclosed by a protective shell 7 of glass, metal, ceramics or the like, which in turn is surrounded by a protection sheath 8 of plastics material which is preferably shrunk-on.

The barrel 1 terminates proximally in an elongated insulating strengthening cylinder 9 which is of greater dimensions or thickness than that of the barrel proper 1 and also enclosed by the sheath 8. At a short distance from its proximal end, the barrel 1 is provided with an HF connection 10 having an insulated lower portion.

Proximally of the end of the barrel proper, the strengthening cylinder 9 is provided with an elongated cavity or elongated outwardly open recess 11 which is covered over by the sheath 8. In this recess is arranged an insulating body 12 which has restricted axial movement and which is provided at its two ends with bores containing oppositely directed threads into which the ends 2b and 2c of the traction rod parts 2, 2a, which is divided at this point, are screwed by means of external threads which are also oppositely directed, with the result that end part 2a of the traction rod is fully insulated from the part 2 of the traction rod which is connected to the HF terminal via barrel 1. The cylindrical insulating body 12 is provided with radial bores 13 distributed around its periphery into which a spigot may be inserted so that the body 12 can be rotated and thus a screwed connection obtained to the ends 2b and 2c of the divided traction rod.

Figure 5:
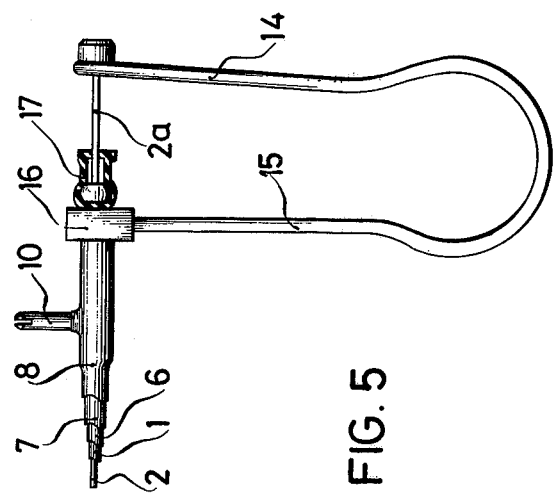

The proximal part 2a of the traction rod is connected to the movable limb 14 of a scissors grip or to a limb 14 of a U-shaped spring grip, FIG. 5, while the other limb 15 is rigidly connected to a head part 16 of the strengthening cylinder 9. To form a seal between the traction rod 2a and its guide, part 16 is provided with an olive covered by a rubber cap 17, the perforated proximal wall of the cap then pressing tightly against the traction rod 2a.

By operating the handle 14, 15, the divided traction rod 2, 2a is moved axially to open and close the jaws 4, 5. When this is done no current whatever is transmitted to the handle section and any risk to the doctor performing the treatment is thus ruled out.

Figure 2:
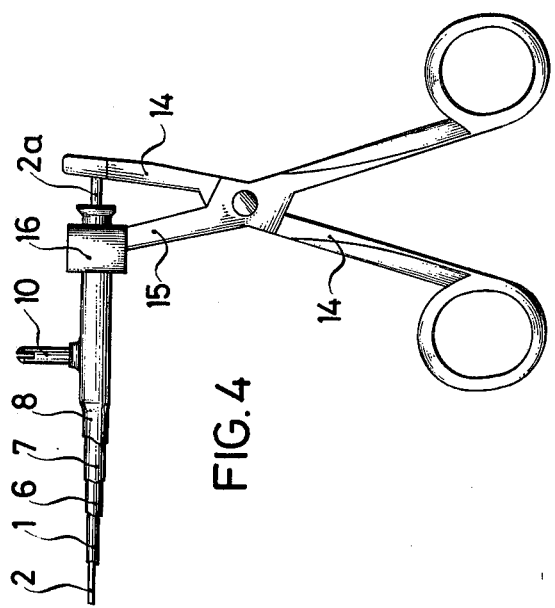
FIG. 2 is an enlarged axial section through the portion X of FIG. 1, outlined in chain lines.
Figure 3:
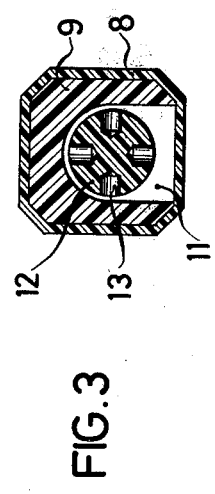
FIG. 3 is a cross-section taken along the line III—III of FIG. 2, FIGS. 4 and 5 are side-views of the proximal part of the coagulation forceps showing modified handles.
Figure 4:
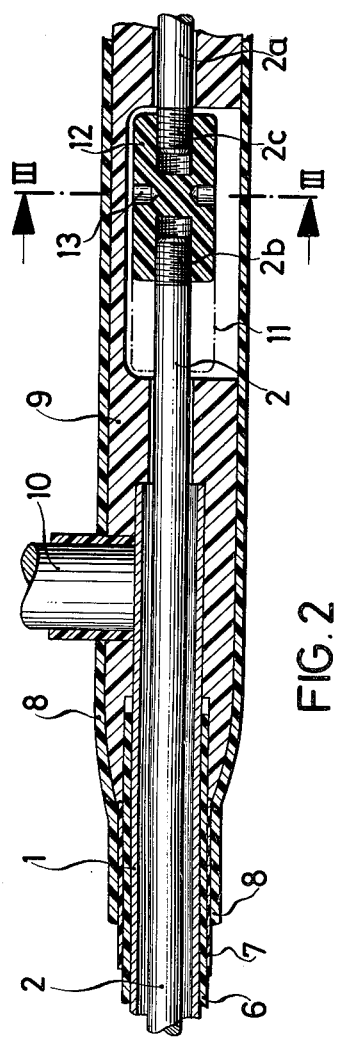
Figure 6:
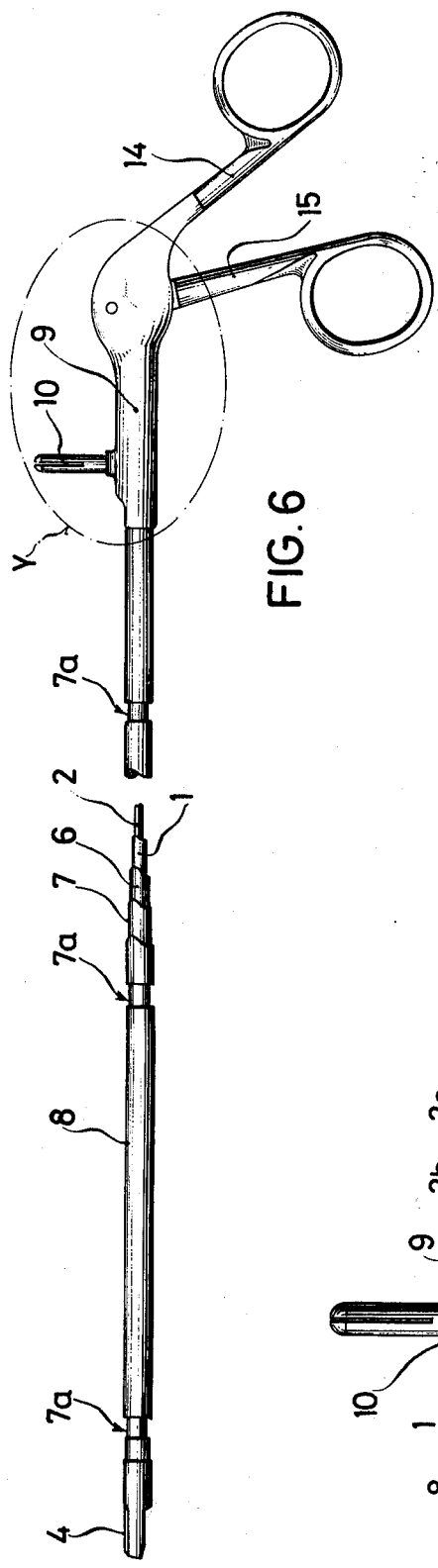
FIG. 6 is a side view corresponding to FIG. 1 showing modified insulation.
Figure 8:
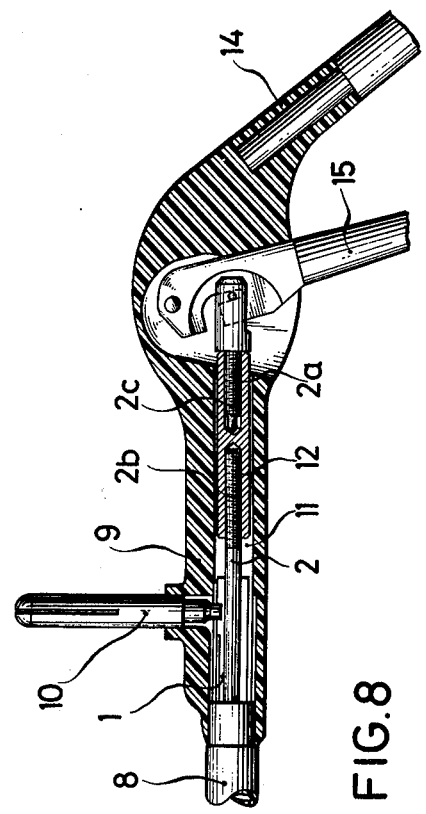
Figure 7:
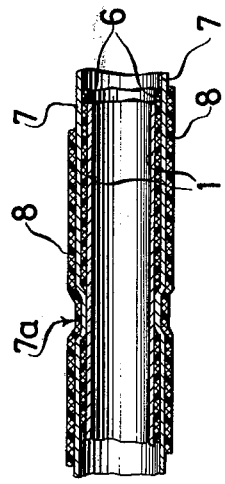
FIG. 7 is a partial axial section through FIG. 6 at a point 7a, FIG. 8 is a longitudinal section through the portion Y circled in FIG. 6.

In a modification of the embodiment of FIGS. 1 and 2 which is shown in FIGS. 6, 7 and 8, the procedure is that in the rigid protective shell 7, which advantageously is of metal, there are a number of spaced interruptions, i.e. the shell is indented, at points 7a for example. At these divisions 7a, the external shrunk-on sheath 8 which is fitted contracts to a greater degree than along the rest of the periphery and is thus particularly firmly seated. As a result of the protective shell 7 being divided or interrupted, the magnitude of the capacitive current flow is cut down and the more divisions there are the greater security there is against flash-over through the outer shrunk-on sheath 8 because the total capacitive currents which occur in the individual sections become almost completely ineffectual.

As shown in FIG. 8, the cavity 11 in the insulating part 9 may also be formed as a cylindrical bore 11 parallel to the axis in which the insulating body 12 for the attachment of the ends 2b, 2c of the traction rod is displaceably mounted.

I claim:

1. A single-pole coagulation forceps instrument for endoscopy, said forceps comprising
   (a) a traction rod having jaw means at one end, and said rod comprising two spaced apart axially aligned parts which are insulatingly interconnected by an insulating body, said jaw means being connected to one of said parts;
   (b) an electrically conductive, externally insulated guide barrel through which said traction rod passes and which includes a connection element connectable to a HF terminal, said jaw means being adjacent one end of said barrel;
   (c) handle means connected to the other of said rod parts for moving said traction rod axially in said barrel for opening and closing said jaw means;
   (d) means electrically connecting said jaw means to said barrel;
   (e) an insulating sleeve secured to the other end of said barrel and having a greater cross-section than that of said barrel, and
   (f) said insulating sleeve defining a cavity which is spaced from said other end of said barrel and in which said insulating body is disposed and is axially displaceable when said traction rod is moved axially by said handle means.

2. A coagulation forceps as claimed in claim 1, wherein said cavity defined by said insulating sleeve is open in a direction towards the exterior of said insulating sleeve and is covered over by an insulating sheath which is shrunk-on said sleeve.

3. A coagulation forceps as claimed in claim 1, wherein said insulating body is of cylindrical form and defines at its opposite ends axial bores having oppositely directed threads, and oppositely facing ends of said parts of said traction rod have oppositely directed threads, said oppositely facing ends being screwed into said axial bores thereby interconnecting said parts of said traction rod.

4. A coagulation forceps as claimed in claim 1, wherein said insulating sleeve includes an enlarged head portion, said handle means comprising a scissors grip handle, one limb of said scissors grip handle being rigidly connected to said head portion, while the other limb of said scissors grip handle engages with the adjacent end of said traction rod.

5. A coagulation forceps as claimed in claim 1, wherein said insulating sleeve includes an enlarged head portion, said handle means comprising a U-shaped spring handle, one limb of said U-shaped spring handle being rigidly connected to said head portion, while the other limb of said spring handle engages with the adjacent end of said traction rod.

6. A coagulation forceps as claimed in claim 1, wherein said guide barrel is surrounded by an insulating sheath in turn surrounded along its length by a rigid protective shell which is indented at a number of spaced locations and onto which an insulating sheath is shrunk.

* * * * *